United States Patent
Pulugurtha et al.

(10) Patent No.: US 11,944,759 B2
(45) Date of Patent: Apr. 2, 2024

(54) CATHETER INCLUDING VARIABLE STRESS RELIEF STRUCTURAL SUPPORT MEMBER

(71) Applicant: Covidien LP, Mansfield, MA (US)

(72) Inventors: Syamala Rani Pulugurtha, Irvine, CA (US); Gopan Patel, Orange, CA (US); Ujwal Jalgaonkar, Irvine, CA (US)

(73) Assignee: Covidien LP, Mansfield, MA (US)

( * ) Notice: Subject to any disclaimer, the term of this patent is extended or adjusted under 35 U.S.C. 154(b) by 282 days.

(21) Appl. No.: 17/308,783

(22) Filed: May 5, 2021

(65) Prior Publication Data
US 2022/0355067 A1    Nov. 10, 2022

(51) Int. Cl.
*A61M 25/00*    (2006.01)

(52) U.S. Cl.
CPC ...... *A61M 25/005* (2013.01); *A61M 25/0012* (2013.01); *A61M 2205/0266* (2013.01)

(58) Field of Classification Search
CPC ............ A61M 25/005; A61M 25/0012; A61M 25/0045; A61M 25/008; A61M 25/0052; A61M 2205/0266; A61M 2205/0063; A61M 2205/0059
See application file for complete search history.

(56) References Cited

U.S. PATENT DOCUMENTS

| | | | | |
|---|---|---|---|---|
| 5,514,115 A | * | 5/1996 | Frantzen | A61M 25/0144 606/78 |
| 6,159,187 A | * | 12/2000 | Park | A61M 25/0041 604/523 |
| 6,540,849 B2 | | 4/2003 | DiCarlo et al. | |
| 2004/0116833 A1 | * | 6/2004 | Kato | D07B 5/005 600/585 |
| 2004/0181208 A1 | | 9/2004 | Poole | |
| 2013/0079746 A1 | | 3/2013 | Fischell et al. | |
| 2014/0378916 A1 | * | 12/2014 | Simpson | A61M 25/0043 604/264 |
| 2016/0271362 A1 | * | 9/2016 | Van Liere | A61M 25/0053 |
| 2017/0113018 A1 | | 4/2017 | Shimizu et al. | |
| 2018/0310957 A1 | | 11/2018 | Cise et al. | |

OTHER PUBLICATIONS

Extended Search Report from counterpart European Application No. 22171714.3 dated Oct. 12, 2022, 10 pp.
"Introduction to Nitinol" SAES Group, Memry Corporation 2017, 41 pages, retreived from memry.com.
Miyazaki et al., "Effects of Several Factors on the Ductility of the Ti—Ni Alloy" Martensitic Transformations II (ed.) B.C. Muddle, Materials Science Forum, 1990, vols. 56-58, pp. 765-770.

(Continued)

*Primary Examiner* — Chelsea E Stinson
*Assistant Examiner* — Anh Bui
(74) *Attorney, Agent, or Firm* — Shumaker & Sieffert, P.A.

(57) ABSTRACT

In some examples a catheter includes an inner liner, an outer jacket, and a structural support member positioned between at least a portion of the inner liner and at least a portion of the outer jacket. A first portion of the structural support member has a first residual stress and a second portion of the structural support member has a second residual stress, greater than the first residual stress. The second portion of the structural support member includes a percent cold work greater than about 20%.

20 Claims, 4 Drawing Sheets

(56) References Cited

OTHER PUBLICATIONS

Drexel et al."The Effects of Cold Work and Heat Treatment on the Properties of Nitinol Wire" Proceedings of the International Conference on Shape Memory and Superelastic Technologies, 2008, pp. 447-454.
"Fetch 2 Aspiration Catheter" Boston Scientific Corporation, Brochure from www.bostonscientific.eu, Jun. 2015, 2 pages.
Khalil, Heidi F., "Changes in the Mechanical Behavior of Nitinol Following Variations of Heat Treatment Duration and Temperature" Georgia Institute of Technology, Dec. 2009, 59 pages.

* cited by examiner

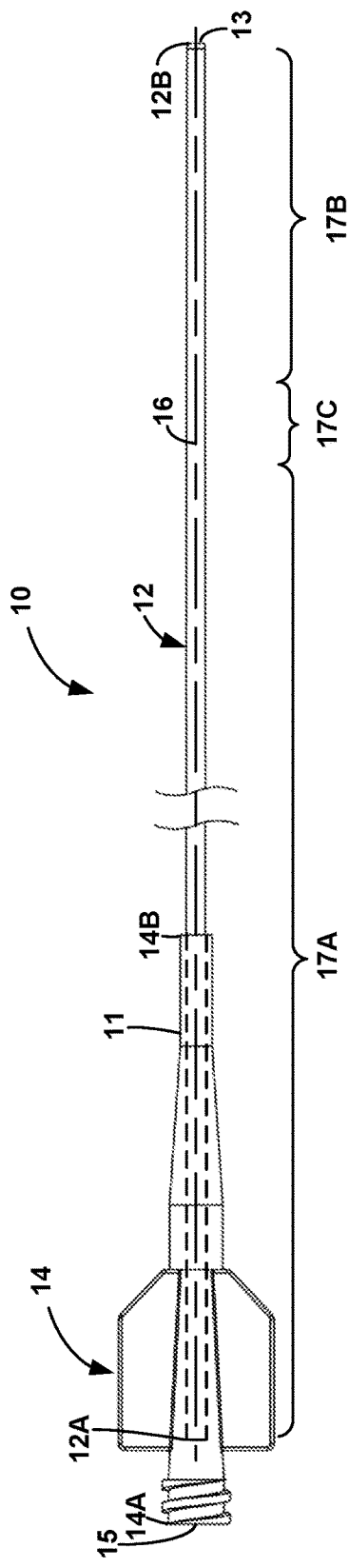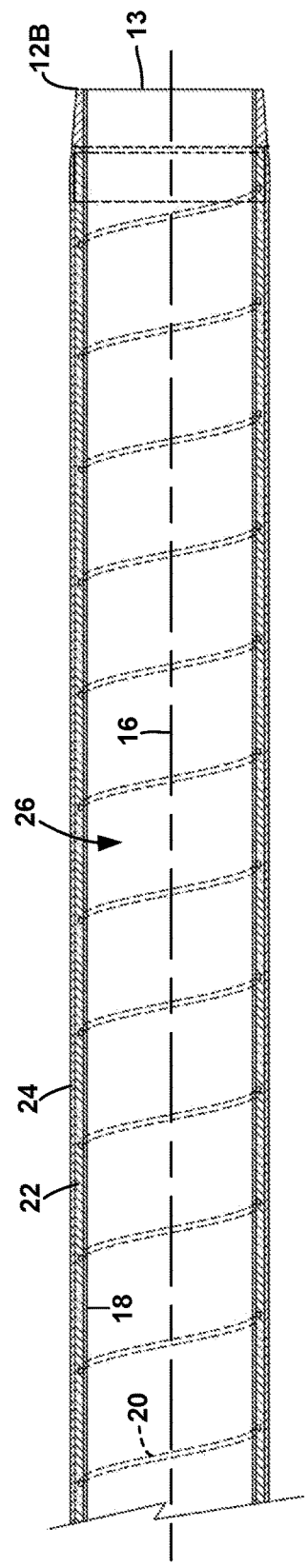

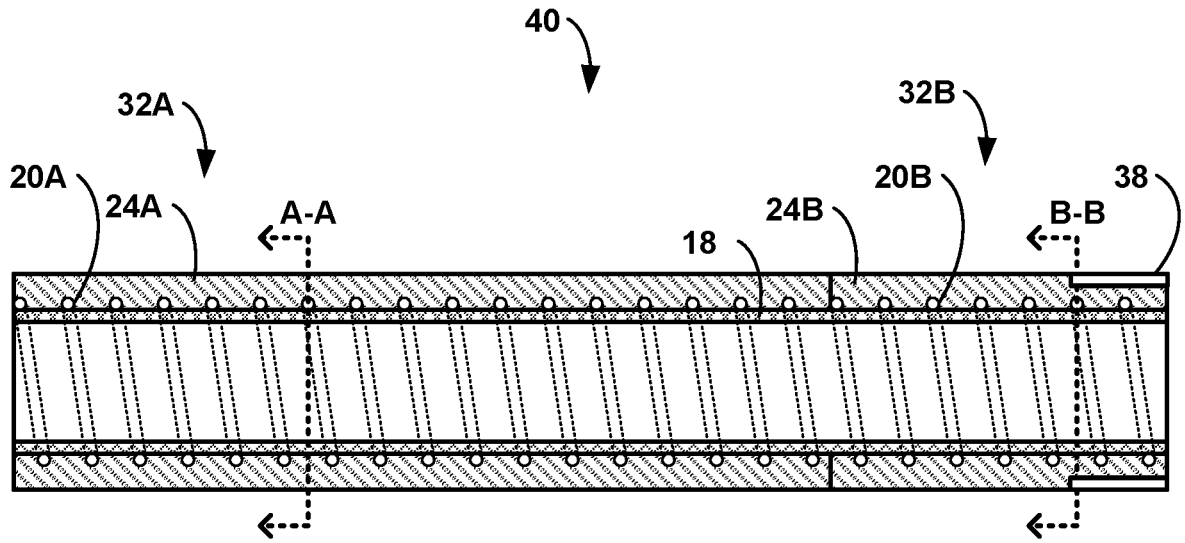
FIG. 5A
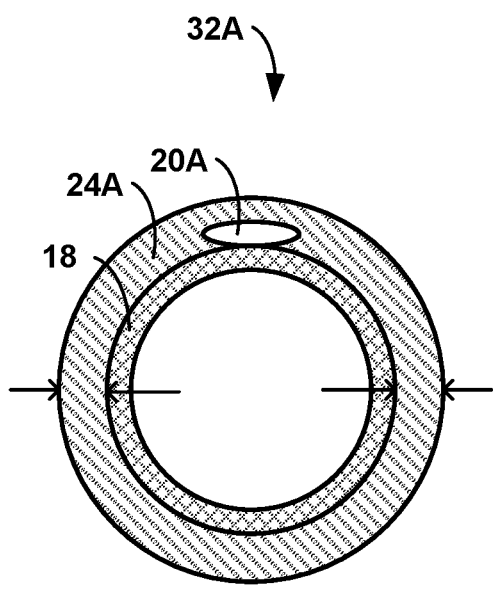 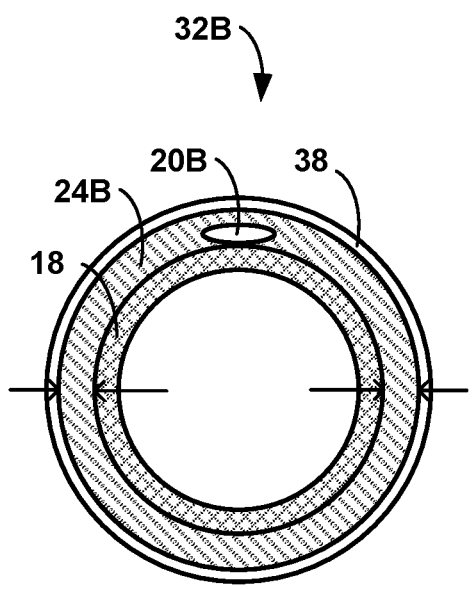
FIG. 5B FIG. 5C

CATHETER INCLUDING VARIABLE STRESS RELIEF STRUCTURAL SUPPORT MEMBER

TECHNICAL FIELD

This disclosure relates to medical catheters and methods of making the same.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters with variable degrees of stress relief along a structural support member, such as a coil or braid, and methods of forming catheters.

In some examples described herein, a catheter includes an inner liner, an outer jacket, and a structural support member positioned between at least a portion of the inner liner and at least a portion of the outer jacket. The structural support member, in combination with the outer jacket, provides the catheter with stiffness and strength for navigating the catheter through vasculature without buckling or kinking. The stiffness and strength of the structural support member is due, at least in part, to cold working of a material, such as nitinol, forming the structural support member, such that the resulting structural support member has residual stress. Stiffness of the structural support member in various portions of the catheter, such as proximal and medial portions of the catheter, may support navigability of the catheter by providing buckling resistance to the catheter as the catheter is pushed through the vasculature. However, stiffness of the structural support member in other portions of the catheter, such as a distal end of the catheter leading traversal of the catheter through the vasculature, may reduce integrity of the catheter by inhibiting positioning of the structural support member during manufacture and/or may inhibit navigability of the catheter by reducing deflection of the corresponding portion of the catheter and increasing a push force of the catheter. As one example, As another example, stiffness at a distal end of the catheter may inhibit deflection and tracking of the leading portion of the catheter through tortuous vasculature.

To provide both relatively high stiffness and strength in some portions of the catheter and greater integrity and/or flexibility in other portions of the catheter, the structural support member has variable stiffness along a longitudinal axis of the catheter. One or more portions of the structural support member are heat treated to relieve stress from cold working and/or increase ductility in the structural support member. In some instances, the heat treatment may be applied to the structural support member while the catheter is partially assembled to increase structural integrity of the catheter and/or reduce or eliminate an adhesive between the structural support member and adjacent components of the catheter. For example, a relatively small diameter structural support member having a large amount of cold work may be heat treated while positioned on an inner liner and prior to application of an outer jacket to reduce a stiffness of the structural support member and better integration of the structural support member within the catheter. In some instances, the heat treatment may be applied to the structural support member before the catheter is fully assembled to permit customizable stiffness of an assembled catheter that may correspond to anticipated conditions encountered in navigating through and/or operating in the vasculature. For example, the relatively high ductility of the one or more portions may enable the distal end of the catheter to more easily navigate through the tortuous vasculature, while the proximal and medial portions of the catheter may continue to provide strength and stiffness to resist kinking. As a result, a corresponding thickness of the outer jacket at the distal end may be reduced, such that additional components, such as a marker band, may be incorporated into the distal end of the catheter without reducing an inner diameter of the catheter or compromising navigability of the catheter.

In some examples, a catheter includes an inner liner, an outer jacket, and a structural support member positioned between at least a portion of the inner liner and at least a portion of the outer jacket. A first portion of the structural support member has a first residual stress and a second portion of the structural support member has a second residual stress, greater than the first residual stress. The second portion of the structural support member includes a percent cold work greater than about 20%.

In some examples, a method for manufacturing a catheter includes heat treating a first portion of a structural support member of an elongated body of the catheter, the elongated body extending between a proximal and a distal end and including an inner liner and the structural support member. The inner liner defines an inner lumen of the elongated body and extends to the distal end of the elongated body. The structural support member is positioned over at least a portion of the inner liner. After heat treating, the first portion of the structural support member has a first residual stress and a second portion of the structural support member has a second residual stress, greater than the first residual stress.

This disclosure also describes examples of methods of using the catheters.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

FIG. 1 is a side elevation view of an example catheter, which includes a catheter body and a hub.

FIG. 2 is a conceptual cross-sectional view of a part of the catheter body of FIG. 1, where the cross-section is taken through a center of the catheter body and along a longitudinal axis of the catheter body.

FIG. 5A is a conceptual cross-sectional view of a part of a catheter body including a variable stiffness structural support member, where the cross-section is taken through a center of the catheter body and along a longitudinal axis of the catheter body.

FIG. 5B is a conceptual cross-sectional view of the catheter body of FIG. 5A taken along line A-A in FIG. 5A.

FIG. 5C is a conceptual cross-sectional view of the catheter body of FIG. 5A taken along line B-B in FIG. 5A.

DETAILED DESCRIPTION

Figure 3:
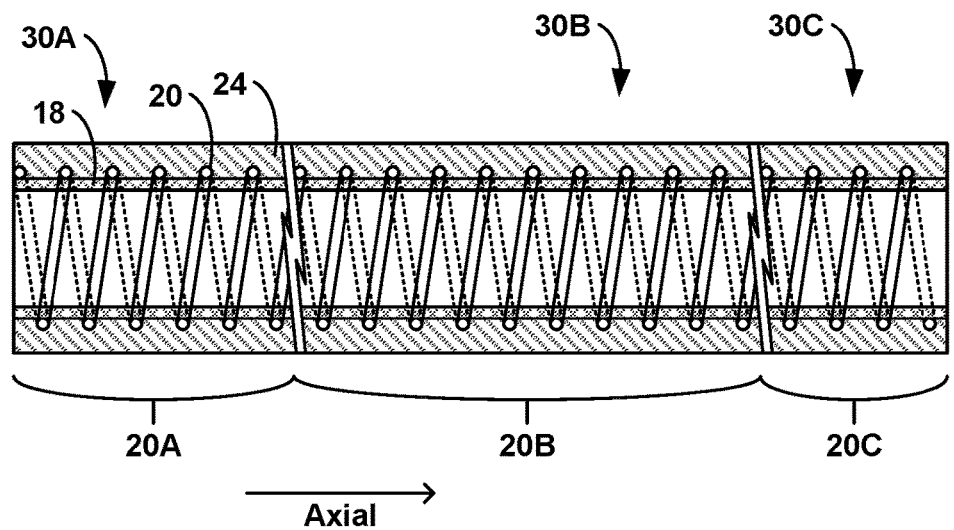
FIG. 3 is a conceptual cross-sectional view of a portion of a catheter body including a coiled structural support member, where the cross-section is taken through a center of the catheter body and along a longitudinal axis of the catheter body.

The disclosure describes a catheter that includes a relatively flexible catheter body that is configured to be navigated through vasculature of a patient with increased navigability.

Catheters may be used to diagnose and treat a variety of conditions, including thrombosis. For example, thrombosis occurs when a thrombus (e.g., a blood clot or other embolus) forms and obstructs vasculature of a patient. In some medical procedures, to treat a patient with thrombosis, a clinician may position an aspiration catheter in a blood vessel of the patient (i.e., catheterization) near the thrombus, apply suction to the aspiration catheter, and engage the thrombus with a tip of the aspiration catheter. This medical procedure may be, for example, A Direct Aspiration first Pass Technique (ADAPT) for acute stroke thrombectomy, or any other aspiration of thrombus or other material from the neurovasculature or other blood vessels. During aspiration, the aspirated thrombus and/or other materials or fluids may flow through the aspiration catheter, and removal of the thrombus may at least partially depend on a flow rate of the aspirated material from the aspiration site. In addition, the aspiration force generated via the aspiration catheter is a function of the inner diameter of the catheter.

In addition to or instead of medical aspiration, a catheter can be used to deliver a therapeutic device to a target treatment site within vasculature (e.g., neurovasculature) of a patient to treat a defect in the vasculature, such as, but not limited to, aneurysms or arteriovenous malformations. The therapeutic neurovascular device may include any suitable medical device configured to be used to treat a defect in vasculature of a patient or used to facilitate treatment of the neurovasculature. For example, the therapeutic device can include a thrombectomy device (e.g. a stent retriever), a flow diverter, a stent, an aspiration catheter, a drug delivery catheter, a balloon catheter, a microvascular plug, a filter, or an implantable medical device, such as an embolic coil.

To position a catheter in a blood vessel of a patient, a clinician may push a proximal portion (e.g., a proximal end) of the catheter to advance the catheter through the blood vessel. Walls of the blood vessel may guide a distal tip (e.g., at a distal end) of the catheter through the blood vessel. However, some blood vessels, such as cerebral arteries, have relatively tortuous configurations. These tortuous configurations may include relatively low radius bends that sharply bend the catheter or create resistance along a longitudinal axis of the catheter. As discussed in further detail below, the catheters described herein enable the catheter to be navigated to a target site within vasculature of a patient e.g., by increasing flexibility of various portions of the structural support member, such as at or near the distal end, by heat treating these various portions to relieve stresses in the structural support member. As a result, the catheters described herein may more easily conform to tortuous vasculature and/or reduce an amount of push force for navigating through the tortuous vasculature. The catheters described herein may also enable the catheter to maintain integrity during navigation to the target site by conforming to an inner liner of the catheter or mandrel used to form the catheter during manufacture, such as at or near the distal end, by heat treating this portion to relieve stresses in the structural support member prior to an outer jacket being formed. As a result, the catheters described herein may better resist delamination forces and maintain integrity in response to bending forces.

In some examples described herein, a catheter includes a structural support member positioned between an inner liner and an outer jacket. During or prior to assembly of the catheter, the structural support member can be heat treated by applying heat to at least a portion of the catheter, such as at or near the distal end. Some heat treatments include heating a portion of the assembled or partially assembled catheter to a temperature that is both sufficiently high to relieve stresses in the corresponding portion of the structural support member and sufficiently low to maintain a structural integrity of the corresponding portions of the adjacent inner liner and outer jacket. By heat treating the structural support member prior to complete assembly of the catheter, the structural support member may conform to and remain positioned on the inner liner during assembly, and therefore may more strongly and/or readily adhere to the outer jacket and/or inner liner, either directly or through an intermediate support layer, such that the structural support member may be less likely to separate from the outer jacket and/or inner liner in response to compression or bending forces experienced while navigating the catheter through the vasculature compared to catheters that do not include a heat-treated structural support member.

In some examples, the heat treatment can be applied to, or in various amounts at, particular portions of the structural support member to relieve stresses and/or increase the ductility of the particular portions of the structural support member. Certain portions of the structural support member may be more likely to experience high degrees of deflection than other portions of the catheter. As one example, during navigation through vasculature of patient, a leading, distal end of the catheter may encounter a sharp turn or constriction that exerts a bending or compressive force on the distal end of the catheter. To navigate through the portion, a clinician may increase a push force on the catheter, which may result in kinking or buckling of the catheter. As another example, during aspiration of a treatment site, a portion of the catheter positioned at a sharp turn or constriction may resist a bending or compressive force on that particular portion of the catheter, which may impede flow of an aspiration fluid. The heat-treated portion of the structural support member may have reduced stresses and/or greater ductility than non-heat-treated or lesser-heat-treated portion of the structural support member, thereby increasing flexibility of the distal end and/or other portions of the catheter. In the examples above, the distal end may more easily deflect and/or conform to the sharp turn or constriction of the vasculature, or the portion of the catheter at the sharp turn or constriction may bend while maintaining a high cross-sectional area through which the aspiration fluid may flow. In some examples, the heat treatment may configure the catheter with a particular stiffness profile and behavior that corresponds to a particular use for the catheter, such as for a known shape of the vasculature for a particular treatment site. As a result, a catheter may be heat treated to produce a catheter with a customized, particular flexibility for the particular application.

In various ways described herein, example catheters may resist temporary (e.g., buckling) or permanent (e.g., delamination) deformation when being navigated through vasculature having tortuous configurations. FIG. 1 is a side elevation view of an example catheter 10, which includes catheter body 12 and hub 14. Catheter hub 14 is positioned at a proximal end of catheter 10 and defines an opening through which an inner lumen 26 (shown in FIG. 2) of catheter body 12 may be accessed and, in some examples, closed. For example, catheter hub 14 may include a luer connector for connecting to another device, a hemostasis valve, or another mechanism or combination of mechanisms. In some examples, catheter 10 includes strain relief member 11, which may be a part of hub 14 or may be separate from hub 14. In other examples, the proximal end of catheter 10 can include another structure in addition or, or instead of, hub 14.

Catheter body 12 is an elongated body that extends from proximal end 12A to distal end 12B and defines at least one inner lumen 26 (e.g., one inner lumen, two inner lumens, or three inner lumens) that terminates at distal opening 13 defined by catheter body 12. In the example shown in FIG. 1, proximal end 12A of catheter body 12 is received within hub 14 and is mechanically or otherwise connected to hub 14 via an adhesive, welding, or another suitable technique or combination of techniques. Opening 15 defined by hub 14 and located at proximal end 14A of hub 14 is aligned with inner lumen 26 of catheter body 12, such that inner lumen 26 of catheter body 12 may be accessed via opening 15.

Catheter body 12 has a suitable length for accessing a target tissue site within the patient from a vascular access point. The length may be measured along longitudinal axis 16 of catheter body 12. The target tissue site may depend on the medical procedure for which catheter 10 is used. For example, if catheter 10 is a distal access catheter used to access vasculature in a brain of a patient from a femoral artery access point at the groin of the patient, catheter body 12 may have a length of about 129 centimeters (cm) to about 135 cm, such as about 132 cm, although other lengths may be used. In other examples, such as examples in which catheter 10 is a distal access catheter used to access vasculature in a brain of a patient from a radial artery access point, catheter body 12 may have a length of about 80 cm to about 120 cm, such as about 85 cm, 90 cm, 95 cm, 100 cm, 105 cm, although other lengths may be used (e.g., sheaths or radial intermediate catheters may be 5-8 cm longer).

Catheter body 12 can be relatively thin-walled, such that it defines a relatively large inner diameter for a given outer diameter, which may further contribute to the flexibility and kink-resistance of catheter body 12. The wall thickness of catheter body 12 may be the difference between the outer diameter of catheter body 12 and the inner diameter of catheter body 12, as defined by inner lumen 26. For example, in some examples, an outer diameter of catheter body 12 may be about 4 French to about 12 French, such as about 5 French or about 6 French. The measurement term French, abbreviated Fr or F, is three times the diameter of a device as measured in mm. Thus, a 6 French diameter is about 2 millimeters (mm), a 5 French diameter is about 1.67 mm, a 4 French diameter is about 1.33 mm, and a 3 French diameter is about 1 mm. The term "about" or "approximately" as used herein with dimensions may refer to the exact numerical value or a range within the numerical value resulting from manufacturing tolerances and/or within 1%, 5%, or 10% of the numerical value. For example, a length of about 10 mm refers to a length of 10 mm to the extent permitted by manufacturing tolerances, or a length of 10 mm+/−0.1 mm, +/−0.5 mm, or +/−1 mm in various examples.

In some examples, rather than being formed from two or more discrete and separate longitudinally extending segments that are mechanically connected to each other, e.g., at axial butt joints, catheter body 12 may be substantially continuous along a length of catheter body 12. For example, catheter body 12 may include an inner liner that defines the inner lumen 26 of catheter body 12 and continuously extends from proximal end 12A to distal end 12B of catheter body 12, and a structural support member that extends across at least a part of the proximal portion 17A, at least part of the distal portion 17B, and the medial portion 17C of catheter body 12. A substantially continuous catheter body 12 may be configured to better distribute forces in a longitudinal direction (in a direction along longitudinal axis 16) and rotational direction (rotation about longitudinal axis 16) compared to a catheter body including two or more longitudinally extending segments that are mechanically connected to each other. Thus, the substantially continuous construction of catheter body 12 may contribute to the ability of body 12 to transfer axial pushing forces from a proximal portion 17A of catheter body 12 to a distal portion 17B, as well transfer rotational forces (if any) applied from proximal portion 17A of catheter body 12 to distal portion 17B. While in some examples, as will be described with reference to FIGS. 5A-5C, catheter body 12 may include an outer jacket formed from two or more longitudinally extending segments that are in an abutting relationship, due to the continuous inner liner and the structural support member that extends along a majority of the length of catheter body 12, catheter body 12 may still better distribute forces and flexibility compared to a catheter body including two or more longitudinal sections that are mechanically connected to each other.

In some examples, at least a portion of an outer surface of catheter body 12 includes one or more coatings, such as, but not limited to, an anti-thrombogenic coating, which may help reduce the formation of thrombi in vitro, an antimicrobial coating, and/or a lubricating coating. The lubricating coating may be configured to reduce static friction and/kinetic friction between catheter body 12 and tissue of the patient as catheter body 12 is advanced through the vasculature. The lubricating coating can be, for example, a hydrophilic coating. In some examples, the entire working length of catheter body 12 (from distal end 14B of hub 14 to distal end 12B) is coated with the hydrophilic coating. In other examples, only a portion of the working length of catheter body 12 coated with the hydrophilic coating. This may provide a length of catheter body 12 distal to distal end 14B of hub 14 with which the clinician may grip catheter body 12, e.g., to rotate catheter body 12 or push catheter body 12 through vasculature.

As described in further detail below, catheter body 12 may be used to access relatively distal locations in a patient, such as the middle cerebral artery (MCA) in a brain of a patient. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists and/or turns) through the vasculature to reach these tissue sites. Catheter body 12 may be structurally configured to be relatively flexible, pushable, and kink- and buckle-resistant, so that it may resist buckling when a pushing force is applied to a relatively proximal portion of catheter 10 to advance the catheter body 12 distally through vasculature and/or resist kinking when traversing around a tight turn in the vasculature. For example, kinking or buckling may occur when a portion of a catheter body undergoes deformation along (e.g., buckling) or away from (e.g., kinking) a longitudinal axis of the catheter in response to a bending or compressive force. The bending or compressive force may result from the leading distal end of the catheter catching against a bend or other tortuous configuration, or a portion of the catheter experiencing a high amount of friction against a bend or other tortuous configuration. Kinking and/or buckling of catheter body 12 may hinder a clinician's efforts to push the catheter body distally, e.g., past a turn.

One characteristic that may contribute to at least the pushability, navigability, and/or flexibility of catheter body 12 is flexibility of the structural support member in certain portions of the catheter that navigate through or are positioned within particularly tortuous vasculature. In accordance with examples of this disclosure, at least a portion of the structural support member can be heat treated to relieve stresses (e.g., due to cold working) of the portion of the structural support member. The heat-treated portion of the structural support member may more readily deflect along or conform to tortuous vasculature, thereby increasing navigability through the vasculature and resisting kinking or buckling due to compression or bending. This increased flexibility may be particularly useful for portions of the structural support member that correspond to sections of the catheter that may be configured to lead navigation through tortuous vasculature or position within tortuous vasculature. For example, a distal portion of the catheter may experience more tortuous vasculature than more proximal or medial portions of the catheter.

Any of the characteristics described herein that may contribute to at least the pushability, navigability, and/or flexibility of catheter body 12 may be used alone or in combination with each other.

FIG. 2 is a conceptual cross-sectional view of a part of catheter body 12 including distal end 12B, where the cross-section is taken through a center of catheter body 12 along longitudinal axis 16. As illustrated in the quad-layer configuration of FIG. 2, catheter body 12 includes inner liner 18, structural support member 20, support layer 22, and outer jacket 24; however, in other examples, catheter body 12 may not include support layer 22, such as in a tri-layer configuration as illustrated in FIG. 3 and FIGS. 5A-5C.

Inner liner 18 defines inner lumen 26 of catheter body 12, inner lumen 26 extending from proximal end 12A to distal end 12B and defining a passageway extending from proximal end 12A to distal opening 13 at distal end 12B of catheter body 12. Inner lumen 26 may be sized to receive a medical device (e.g., another catheter, a guidewire, an embolic protection device, a stent, or any combination thereof), a therapeutic agent, or the like. At least the inner surface of inner liner 18 defining inner lumen 26 may be lubricious in some examples to facilitate the introduction and passage of a device, a therapeutic agent, or the like, through inner lumen 26. For example, the material from which the entire inner liner 18 is formed may be lubricious, or inner liner 18 may be formed from two or more materials, where the material that defines inner lumen 26 may be more lubricious than the material that interfaces with structural support member 20 and support layer 22. In addition to, or instead of, being formed from a lubricious material, in some examples, an inner surface of inner liner 18 is coated with a lubricious coating. Example materials from which inner liner 18 may be formed include, but are not limited to, polytetrafluoroethylene (PTFE), fluoropolymer, perfluoroalkyoxy alkane (PFA), fluorinated ethylene propylene (FEP), or any combination thereof. For example, inner liner 18 may be formed from an etched PTFE, e.g., may consist essentially of an etched PTFE.

Outer jacket 24 is positioned radially outward of inner liner 18 and structural support member 20, and, in some examples, defines an outer surface of catheter body 12. Although a coating or another material may be applied over the outer surface of outer jacket 24, outer jacket 24 may substantially define a shape and size of the outer surface of catheter body 12. Outer jacket 24, together with structural support member 20 and inner liner 18, may be configured to define catheter body 12 having the desired flexibility, kink resistance, and pushability characteristics. Outer jacket 24 may have stiffness characteristics that contribute to the desired stiffness profile of catheter body 12. For example, outer jacket 24 may be formed to have a stiffness that decreases from a proximal portion 17A of catheter body 12 to a distal portion 17B. In some examples, outer jacket 24 may be formed from two or more different materials that enable outer jacket 24 to exhibit the desired stiffness characteristics, such as may described further in FIGS. 5A-5C below.

The flexibility of outer jacket 24 may be, at least in part, a function of a composition, a hardness (e.g., durometer), and/or a thickness of outer jacket 24. For example, a higher durometer may result in less compressibility and a lower degree of flexibility. To configure catheter body 12 with a particular flexibility profile (e.g., a flexibility along longitudinal axis 16), outer jacket 24 may include multiple outer jacket segments that include varied properties and are supported by a variable heat treated (e.g., with variable stress relief and/or variable ductility) structural support member 20. Example materials from which outer jacket may be formed include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer or other thermoplastic material, or combinations thereof.

Structural support member 20 is configured to increase the structural integrity of catheter body 12 while allowing catheter body 12 to remain relatively flexible. For example, structural support member 20 may be configured to help catheter body 12 substantially maintain its cross-sectional shape or at least help prevent catheter body 12 from buckling or kinking as it is navigated through tortuous anatomy. Structural support member 20, together with inner liner 18, outer jacket 24, and optionally support layer 22, may help distribute both pushing and rotational forces along a length of catheter body 12, which may help prevent kinking of body 12 upon rotation of body 12 or help prevent buckling of body 12 upon application of a pushing force to body 12. As a result, a clinician may apply pushing forces, rotational forces, or both, to proximal portion 17A of catheter body 12, and such forces may cause distal portion 17B of catheter body 12 to advance distally, rotate, or both, respectively. In the example shown in FIG. 2, structural support member 20 extends along only a portion of a length of catheter body 12; however, in other examples, structural support member 20 may extend along an entire length of catheter body 12.

In some examples, structural support member 20 includes a generally tubular braided structure, a coil member defining a plurality of turns (e.g., as illustrated by portion 30 of catheter body 12 in FIG. 3), or both a braided structure and a coil member. Thus, although examples of the disclosure may describe structural support member 20 as a coil, in some other examples, the catheter bodies described herein may include a braided structure instead of a coil or a braided structure in addition to a coil. For example, a proximal portion of structural support member 20 may include a braided structure and a distal portion of structural support member 20 may include a coil member, or vice versa. Structural support member 20 can be made from any suitable material, such as, but not limited to, a metal (e.g., a nickel titanium alloy, stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 20 may include one or more metal wires braided or coiled around inner liner 18. The metal wires may include round wires, flat-round wires, flat wires, or any combination thereof.

Structural support member 20 may be coupled, adhered, and/or mechanically connected to at least a portion of an outer surface of inner liner 18 and/or at least a portion of an inner surface of outer jacket 24. In some examples, structural support member 20 may be directly coupled, adhered, and/or mechanically connected to at least a portion of an outer surface of inner liner 18 and/or at least a portion of an inner surface of outer jacket 24. For example, while catheter 10 of FIG. 2 illustrates a quad-layer configuration that includes support layer 22, in some examples, such as illustrated in FIG. 3 and FIGS. 5A-5C, catheter 10 may include a tri-layer configuration that does not include support layer 22. In such examples, the inner surface of outer jacket 24 and the outer surface of inner liner 18 may, at least partly, directly contact and/or adhere to each other between braids or coils of structural support member 20.

In other examples, such as illustrated in FIG. 2, structural support member 20 may be indirectly coupled, adhered, and/or mechanically connected to at least a portion of the outer surface of inner liner 18 and/or at least a portion of the inner surface of outer jacket 24 via support layer 22. For example, support layer 22 may be a thermoplastic material or a thermoset material, such as a thermoset polymer and/or a thermoset adhesive. In some examples, support layer 22 is positioned between the entire length of structural support member 20 and inner liner 18, while in other examples, support layer 22 is only positioned between a part of the length of structural support member 20 and inner liner 18.

In example catheters that do not include support layer 22, such as illustrated in FIG. 3 and FIGS. 5A-5C, outer jacket 24 may be configured to fill at least part of the spaces (e.g., part or all of the spaces) between portions of structural support member 20, e.g., the spaces between turns of structural support member 20 in examples in which member 20 is a coil member or the spaces defined between pics of a braid. In example catheters that include support layer 22, support layer 22 may be configured to fill at least part of the spaces between portions of structural support member 20.

In some instances, the presence of outer jacket 24 and/or support layer 22 between turns of member 20 may help adhere outer jacket 24 and inner liner 18 to each other and securely integrate structural support member 20 into catheter body 12, such that structural support member 20 may resist detachment during bending or compression of catheter 10. For example, at least by minimizing or even eliminating voids between turns of structural support member 20, such as may be caused by insufficient flow of a material of outer jacket 24, outer jacket 24 and/or support layer 22 may provide a higher contact surface between inner liner 18 and outer jacket 24, which may better distribute pushing or torqueing forces applied to proximal portion 17A of catheter body 12 to distal portion 17B. In addition or instead, minimizing or even eliminating voids between turns of structural support member 20 may provide longitudinal support to structural support member 20 to secure structural support member within catheter body 12.

In some instances, the presence of outer jacket 24 and/or support layer 22 between turns of member 20 may help distribute the flexibility provided by member 20 along the length of member 20, which may help prevent catheter body 12 from kinking. For example, at least by eliminating voids between turns of structural support member 20, outer jacket 24 and/or support layer 22 may transfer the flexing motion from structural support member 20 along a length of catheter body 12. In some examples, support layer 22 has a thickness (measured in a direction orthogonal to longitudinal axis 16) that is greater than or equal to a cross-sectional dimension of the wire that forms the member 20, such that layer 22 is at least partially positioned between outer jacket 24 and structural support member 20. In other examples, support layer 22 has a thickness that is less than or equal to a cross-sectional dimension of the wire that forms the structural support member 20, such that support layer 22 is not positioned between outer jacket 24 and structural support member 20.

In the example illustrated in FIG. 2, structural support member 20 is formed from a wire, such as a rounded (in cross-section) wire, that is shaped to define a coil. In other examples, member 20 may be formed, at least in part, from a flat (in cross-section) wire that is shaped to define a coil. A rounded wire may define a coil member having a lower surface area than a flat wire, such that, for a given length of structural support member 20, inner liner 18 and/or outer jacket 24 may have a higher contact area between coils of structural support member 20. A flat wire may define a coil member having a higher surface area than a round wire, such that, for a given length of structural support member 20, structural support member 20 may have a higher contact area with inner liner 18 and/or outer jacket 24.

The wire from which member 20 is formed can be a metal wire. In some examples, the wire is formed from a shape memory material, such a nickel titanium alloy (Nitinol). In other examples, the wire is formed from stainless steel. In some cases, a nickel titanium alloy may be more crush resistant than stainless steel, and, therefore, may be used to form a structural support member 20 of a catheter that is more resistant to kinking and buckling compared to stainless steel. In addition, as described in further detail below, a shape memory material may allow structural support member 20 to be formed before it is positioned over inner liner 18. For example, the pitch and diameter of member 20 may be defined before member 20 is positioned over inner liner 18, which may provide certain advantages (discussed below). In contrast, when member 20 is formed from stainless steel, the pitch and diameter of member 20 may be defined as member 20 is wound over inner liner 18.

In some examples, structural support member 20 may include a cold worked metal, such as a cold worked metal wire. A cold worked metal may include any metal or alloy that has been, or is capable of being, cold worked. Cold working may involve any forming process in which a metal is shaped at a temperature below a recrystallization temperature of the metal. As a result of cold working, grains of the crystals in the metal may distort according to the shaping directions and flow of the metal, increasing a stiffness and tensile strength of the metal and leaving residual stress in the metal. In the example of structural support member 20, a cold worked metal wire may result in structural support member 20 having increased stiffness and tensile strength compared to a similar structural support member formed from a metal wire that has not been cold worked (e.g., formed from hot working processes). In some example, cold working in structural support member 20 may be expressed as a percent (%) cold work, which may represent a degree of plastic deformation of a metal during cold working. In some examples, at least a portion of structural support member 20 may have between about 20% and about 60% cold work. In some examples, structural support member 20 may include varying degrees of cold work, as will be described further below. For example, one or more portions of structural support member 20 may be heat treated to reduce stress in structural support member 20. In some examples, after cold working and before heat treating, the amount of cold work may be substantially the same along structural support member 20, while in other examples, the amount of cold work may vary along structural support member 20.

In some examples, structural support member 20 includes multiple, longitudinally adjacent structures (e.g., connected to each other, abutting but not connected to each other, or with a gap therebetween). In other examples, structural support member 20 is formed from a single continuous wire that defines a coil member that may include varied properties, such as changes in outer diameter and inner diameter of structural support member 20, changes in outer diameter of the coil member, and/or changes in pitch along the length of member 20. The single wire may be seamless (or joint-less) in that there are no joints (e.g., butt joints) between separate portions of wire that are connected together to define a longer wire; rather, the wire has a unitary body construction. In some examples, a contemporaneous change in pitch and inner and outer diameters of the structural support member 20 including a single, seamless wire may be made possible, at least in part, by a shape memory material from which the wire is formed. Defining structural support member 20 from a single, seamless wire may increase the structural integrity of catheter body 12 compared to examples in which member 20 is formed from multiple wires that are joined together. For example, the joints between wires may adversely affect the tensile strength or lateral flexibility of member 20, which may adversely affect the flexibility and pushability of catheter body 12.

In examples in which structural support member 20 includes a coil (e.g., a helical coil), the flexibility of structural support member 20 may be, at least in part, a function of a pitch of the coil. For a given wire, a larger pitch results in larger gaps between adjacent turns of the wire forming member 20 and a higher degree of flexibility. The pitch can be, for example, the width of one complete turn of wire, measured in a direction along longitudinal axis 16. In some examples, a pitch of structural support member 20 varies along a length of structural support member 20, such that a stiffness (or flexibility) varies along the length. The pitch may continuously vary along the length of member 20, or may progressively change, e.g., include different sections, each section having a respective pitch.

As described above, various components of catheter body 12, such as inner liner 18, structural support member 20, support layer 22, and/or outer jacket 24 may be configured to provide flexibility to catheter body 12. A particular portion of catheter body 12 may have a desired flexibility, such that various compositions and properties of inner liner 18, structural support member 20, support layer 22, and/or outer jacket 24 may be selected and/or configured to achieve, in combination, the desired flexibility. As one example, a portion of catheter body 12, such as distal end 12B, may include a radiopaque marker or other component that may reduce flexibility of the portion of catheter body 12, such as by replacement of a portion of catheter body 12 with a material that has reduced flexibility. As another example, catheter body 12 may be navigated through particularly tortuous vasculature, for which a higher desired flexibility may be desired. To at least partly compensate for this reduced flexibility or increased tortuosity, structural support member 20 may be configured with one or more properties configured to increase flexibility of catheter body 12 compared to a similar structural support member 20 that is not configured with the one or more properties.

In some examples, at least a portion of structural support member 20 is heat treated. A portion of structural support member 20 that has been heat treated may include different properties related to flexibility of catheter body 12 than a non-heat-treated portion of structural support member 20, such as reduced residual stress and/or increased ductility of structural support member 20. These portions of structural support member 20 may be more flexible compared to a similar, but untreated, structural support member. As a result, structural support member 20 may be more flexible at the heat-treated portions of catheter 10, such as at distal end 12B. Example heat treatments that may be used include, but are not limited to, annealing, aging, quenching, or the like, and combinations thereof.

As one example, residual stress may represent an amount of stress in structural support member 20 due to cold working or other processing, and may influence properties such as springback or other properties related to an ability of structural support member 20 to conform against a subassembly, such as inner liner 18 and/or a mandrel over which structural support member 20 is positioned, during assembly of catheter 10. Residual stress in structural support member 20 may be reduced by heat treating structural support member 20 to a temperature that is high enough to relieve at least a portion of the residual stress, while remaining below the recrystallization temperature of structural support member 20, such that structural support member 20 may have reduced springback while retaining a similar microstructure and/or mechanical properties, such as tensile strength, relatively unchanged.

As another example, ductility may represent a degree to which structural support member 20 may undergo plastic deformation under tensile stress before breaking, such as tensile stresses encountered by structural support member 20 in response to deflection during navigation of catheter 10. Ductility may be increased by heat treating structural support member 20 to a temperature that is above the recrystallization temperature of structural support member 20, such that structural support member 20 may undergo increased plastic deformation prior to breaking. Other properties of structural support member 20, such as a grain size or a tensile strength, may also be affected by heat treating above the recrystallization temperature.

In the example of FIG. 2, prior to heat treatment, structural support member 20 may have a relatively uniform percent cold work, ductility, and tensile stress. For example, structural support member 20 may have a relatively high amount of cold work, a relatively high tensile strength, and a relatively low ductility. After heat treatment, one or more portions of structural support member 20 may have a reduced amount of cold work, a reduced elastic modulus, an increased elongation at fracture, a reduced tensile strength, and/or an increased ductility compared to the pre-heat-treated structural support member 20. As one example, after a heat treatment configured to reduce residual stresses, one or more portions of structural support member 20 may have relatively low springback. As another example, after a heat treatment configured to increase ductility, one or more portions of structural support member 20 may have relatively high stiffness for supporting catheter body 12, while one or more portions of structural support member 20 may have relatively high ductility for navigating catheter body 12.

Decreased residual stresses of one or more portions of structural support member 20 may be measured and/or quantified in one or more of a variety of ways including, but not limited to, deformation (or strain release) at fracture, diffraction of electromagnetic radiation, and any other measure of an amount of residual stress (or change in residual stress) prior to or at fracture. For example, structural support member 20 may undergo one or more fracture tests to determine a fracture deformation, one or more electromagnetic tests (e.g., x-ray) to determine an extent of diffraction, and/or other properties related to presence or change of residual stress of structural support member 20.

Increased ductility of one or more portions of structural support member 20 may be measured and/or quantified in one or more of a variety of ways including, but not limited to, percent elongation (or strain) at fracture, reduction of area at fracture, and any other measure of plastic deformation prior to or at fracture. For example, structural support member 20 may undergo one or more tensile tests to determine a fracture strain, one or more lengths of structural support member 20 or a portion of structural support member 20, one or more cross-sectional areas of structural support member 20, and/or other properties related to plastic deformation of structural support member 20 under tensile stress.

In some examples, one or more portions of structural support member 20 may have increased percent elongation at fracture compared to a portion of a similar structural support member that does not include a heat treatment. In some examples, a percent elongation at fracture of a portion of structural support member 20 may be at least about 20% greater than or equal to a percent elongation at fracture of a portion of a similar structural support member that does not include the heat treatment, such as a different portion of structural support member 20 that is untreated. In some examples, one or more portions of structural support member 20 may have increased reduction in area at fracture compared to a portion of a similar structural support member that does not include a heat treatment. In some examples, a reduction of area at fracture of a portion of structural support member 20 may be at least about 10% less than a reduction of area at fracture of a portion of a similar structural support member that does not include the heat treatment, such as a different portion of structural support member 20 that is untreated.

In some examples, heat treatment of one or more portions of structural support member 20 may involve heating the one or more portions of structural support member 20 to a heat treatment temperature, maintaining the one or more portions of structural support member 20 at or above the heat treatment temperature for a period of time, and optionally cooling the one or more portions of structural support member 20. In some examples, the heat treatment temperature may be greater than about 300° C. In some examples, the heat treatment may include annealing. Annealing includes any heat treatment that involves heating up to and maintaining a temperature of a portion of structural support member 20 above a recrystallization temperature of a material of structural support member 20 for a period of time. While not being limited to any particular theory, mechanical working of a material, such as cold working of a nickel titanium alloy, may introduce dislocations into the material. During annealing, atoms may migrate from existing grain boundaries and form new grain boundaries upon recrystallization. As a result of annealing, an annealed portion of structural support member 20 may have a higher ductility and/or lower hardness than a portion of a similar structural support member (e.g., another portion of structural support member 20) that is not annealed or annealed to a lesser extent.

In some examples, the heat treatment may involve other heat treatment that involve temperatures below a recrystallization temperature of a material of structural support member 20. While the relatively high temperatures experienced during annealing may expedite migration of atoms from existing grain boundaries, lower temperatures may still cause migration of atoms, albeit at a lower rate. For example, structural support member 20 formed from nitinol (recrystallization temperature of between about 450° C. and about 550° C.) may be heat treated at temperatures below 450° C., such as about 300° C., to increase percent elongation and/or reduction in area at fracture of the portion of structural support member 20.

In some examples, the heat treatment may be applied to one or more portions of structural support member 20 after catheter 10 is formed, such as after structural support member 20 has been positioned on inner liner 18. As such, various components of catheter body 12 exposed to the heat treatment may be configured to maintain structural integrity at the heat treatment temperature of structural support member. For example, structural support member 20 may be heat treated while positioned on a mandrel and without any contact with a component of catheter 10, such that structural support member 20 may be heat treated at temperatures that may otherwise cause degradation of constituent components of catheter 10.

In some examples, at least a portion of inner liner 18, support layer 22, and/or outer jacket 24 may be formed from a material having a relatively high thermal degradation temperature. For example, as will be described further below, structural support member 20 may be heat treated after positioning structural support member 20 on inner liner 18. During heat treatment, heat may be applied to structural support member 20. To maintain a structural integrity of catheter body 12 during heat treatment, portions of inner liner 18, and/or support layer 22 subject to or adjacent to heat treatment may be formed from materials having a thermal degradation temperature above a heat treatment temperature of structural support member 20. A thermal degradation temperature may be a temperature at which a structural integrity of inner liner 18 and/or support layer 22 may substantially decrease, such as through depolymerization or chain scission. In some examples, a thermal degradation temperature may be a temperature at which a material of inner liner and/or support layer 22 begins to break down.

In some examples, inner liner 18, support layer 22, and/or outer jacket 24 may be formed from materials having a thermal degradation temperature that is greater than a recrystallization temperature of a material of structural support member 20. For example, as described above, structural support member 20 may be heated above the recrystallization temperature to anneal the portion of structural support member 20.

In some examples, the heat treatment can be applied to one or more particular portions of structural support member 20 to increase flexibility of the corresponding portion of catheter body 12. These one or more portions that are heat treated can be certain portions of structural support member 20 that may be more likely to experience stresses that can cause deflection or other deformation than other portions of structural support member 20. For example, a first portion of structural support member 20, such as a more distal portion that may experience a higher degree of tortuosity that more proximal portions, may be heat treated, and a second portion of structural support member 20, such as a more proximal portion, may not be heat treated. As a result, the first portion of structural support member 20 may have different properties than the second portion of structural support member 20. For example, the first portion of structural support member 20 may have a first amount of residual stress and the second portion of structural support member 20 may have a second amount of residual stress that is less than the first amount of residual stress.

In some examples, one or more portions of structural support member 20 that may be subject to relatively high deformation during navigation to a treatment site may be heat treated. For example, a first portion of structural support member 20 near distal opening 13 may be subject to relatively high compressive and/or lateral forces while navigating through tortuous vasculature compared to a more proximal second portion of structural support member 20. To increase flexibility of the first portion of structural support member 20, the first portion of structural support member 20 may be heat treated to increase an amount of residual stress or ductility of the first portion of structural support member 20, such that the first portion of structural support member 20 may more easily navigate through the vasculature. On the other hand, the more proximal second portion of structural support member 20 may still be subject to compressive forces that result from pushing forces on catheter body 12. To maintain stiffness of the second portion of structural support member 20, the second portion of structural support member 20 may not be heat treated, or may be heat treated to a lesser extent than the first portion of structural support member 20. In some examples, a distal portion of structural support member 20 may be heat treated, such as a distal-most five centimeters from distal end 12B.

In some examples, one or more portions of structural support member 20 that may be subject to relatively high deformation during treatment may be heat treated. For example, a first portion of structural support member 20 near distal opening 13 may be subject to relatively high lateral forces due to tortuous vasculature near the treatment site compared to a more proximal second portion of structural support member 20 that may be positioned in larger vasculature. During operation of catheter 10 in vasculature, such as during aspiration or other procedure involving fluid flow, flow of a fluid through inner lumen 26 may be restricted due to kinking of catheter body 12. To increase flow of fluid through catheter body 12, the first portion of structural support member 20 may be heat treated to relieve residual stress and/or increase a ductility of the first portion of structural support member 20, such that the first portion of structural support member 20 may more easily conform to the vasculature without kinking.

In some examples, one or more portions of structural support member 20 may be heat treated to permit incorporation of components that may reduce flexibility of catheter body 12. For example, a first portion of structural support member 20 near distal opening 13 may be adjacent to a radiopaque marker or other functional component that has a flexibility lower than support layer 22 and/or outer jacket 24, such that a thickness of outer jacket 24 adjacent to the first portion of structural support member 20 may be less than a thickness of outer jacket 24 adjacent to a second portion of structural support member 20. To compensate for the relatively low thickness of outer jacket 24, the first portion of structural support member 20 may be heat treated, such that the first portion of structural support member 20 has a lower amount of residual stress and/or a higher ductility than the second portion of structural support member 20.

FIG. 3 is a conceptual cross-sectional view of a proximal portion 30A, a medial portion 30B, and a distal portion 30C of an example catheter body (e.g., catheter body 12 of FIG. 2) including a coiled structural support member 20, where the cross-section is taken through a center of the catheter body and along the longitudinal axis (e.g., longitudinal axis 16 in FIG. 1) of the catheter body. While catheter body 12 is primarily referred to in the description of FIG. 3, in other examples, portions 30A, 30B, 30C can be portions of another catheter body. In the example of FIG. 3, the catheter body is a 3-part catheter body including inner liner 18, structural support member 20, and outer jacket 24 without a support layer (e.g., support layer 22 of FIG. 2). Unless otherwise indicated, inner liner 18, structural support member 20, and outer jacket 24 may be similar to inner liner 18, structural support member 20, and outer jacket 24 of FIG. 2, and vice versa.

As described in FIG. 2, structural support member 20 may include two or more portions 20A, 20B, 20C having different properties at least partly as a result of heat treatment of one or more portions structural support member 20. Structural support member 20 includes a proximal portion 20A corresponding to proximal portion 30A, a medial portion 20B corresponding to medial portion 30B, and a distal portion 20C corresponding to distal portion 30C. Each of proximal portion 20A, medial portion 20B, and distal portion 20C have been subject to a different degree of heat treatment. A degree of heat treatment may correspond to whether the respective portion of structural support member 20 was heat treated, a temperature at which the respective portion of structural support member 20 was heat treated, a direction for which the respective portion of structural support member 20 was heat treated, and the like. For example, structural support member 20 may be formed from a metal using cold working, such that a resulting microstructure of each portion 20A, 20B, 20C of structural support member 20 may be relatively uniform. In one example, after one or more degrees of stress-relieving heat treatment, portions 20A, 20B, 20C may have a same microstructure, but different amount of residual stress. In another example, after one or more degrees of annealing heat treatment, portions 20A, 20B, 20C may have different microstructures, resulting in different ductility. In the example of FIG. 3, proximal portion 20A may not be heat treated, medial portion 20B may be heat treated to a greater degree than proximal portion 20A, and distal portion 20C may be heat treated to a greater degree than both proximal portion 20A and medial portion 20B. As a result, proximal portion 20A, medial portion 20B, and distal portion 20C may each have a different amount of residual stress or ductility.

Figure 4:
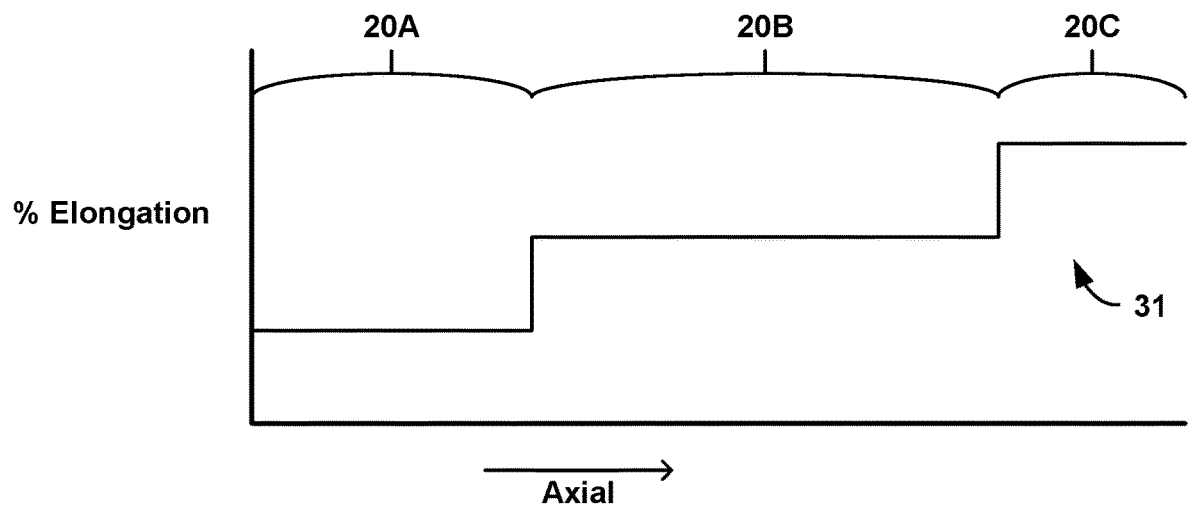
FIG. 4 is a conceptual graph of a heat treatment profile of the portion of the catheter body of FIG. 3 along a longitudinal axis of the catheter body.

FIG. 4 is a conceptual graph of a heat treatment profile 31 of portions 30A, 30B, and 30C of FIG. 3. Heat treatment profile 31 may represent a degree of heat treatment, such as stress-relieving heat treatment or annealing heat treatment, of structural support member 20 of FIG. 3 along a longitudinal axis of catheter body 12. As illustrated in FIG. 4, proximal portion 20A may correspond to a first amount of residual stress or ductility, medial portion 20B may correspond to a second amount of residual stress or ductility, higher than the first amount of residual stress or lower than the first ductility, and distal portion 20C may correspond to a third ductility, higher than both the first and second amounts of residual stress or lower than both the first and second ductilities.

In some examples, a heat treatment profile of a catheter may be configured through heat treatment for a particular application. For example, structural support member 20 in an untreated state may have a relatively high stiffness, such as due to cold working (e.g., drawing) of structural support member 20. For example, an untreated structural support member may have a relatively high stiffness to provide support for portions of a catheter that may be subject primarily compressive forces, such as due to pushing forces. One or more portions of the catheter may be heat treated to generate a heat treatment profile that corresponds to an intended use. For example, a shape or tortuosity of vasculature may vary depending on a treatment site or treatment operation.

In the example of FIG. 4, a manufacturer may provide a heat treatment to catheter body 12 to produce heat treatment profile 31. For example, the manufacturer may intend to navigate catheter body 12 to relatively tortuous vasculature. Heat treatment profile 31 may be configured to resist buckling in a proximal portion of catheter body 12 during positioning of catheter body 12, resist kinking in a medial portion of catheter body 12 during a flow operation involving catheter body 12, and enhance navigability in a distal portion of catheter body 12 during positioning of catheter body 12.

In some examples, catheters described herein may have a flexibility that results from parameters of various components within the catheters, including a variable stiffness of a structural support member resulting from heat treatment of the structural support member, as well as other parameters of materials of the catheter. For example, parameters of inner liner 18, structural support member 20, and/or outer jacket 24 may contribute to flexibility of a catheter.

FIG. 5A is a conceptual cross-sectional view of a portion 40 of a catheter body (e.g., catheter body 12) including a structural support member having portions 20A and 20B (collectively "structural support member 20"), where the cross-section is taken through a center of the catheter body and along a longitudinal axis of the catheter body. Portion 40 of catheter body 12 includes inner liner 18, structural support member 20, and outer jacket 24 (as expressed as portions 24A and 24B). However, in other examples, such as catheter bodies or portions of catheter bodies that include a quad-layer configuration, support layer 22 may be included. Portion 40 includes a proximal portion 32A and a distal portion 32B. FIG. 5B is a conceptual cross-sectional view of proximal portion 32A of portion 40 of catheter body 12 of FIG. 5A taken along line A-A in FIG. 5A, while FIG. 5C is a conceptual cross-sectional view of distal portion 32B of portion 40 of catheter body 12 of FIG. 5A taken along line B-B in FIG. 5A. In the examples of FIG. 5A-5C, outer jacket 24 includes a proximal outer jacket segment 24A and a distal outer jacket segment 24B and structural support member 20 includes a proximal portion 20A and a distal portion 20B.

In some examples, outer jacket 24 may be configured to help provide catheter body 24 with desired flexibility characteristics. Outer jacket 24 includes a plurality of outer jacket segments 24A and 24B. In the example of FIG. 5A, only a first outer jacket segment 24A and a second outer jacket segment 24B are illustrated; however, outer jacket 24 can include any number of outer jacket segments. Segments 24A and 24B can each be, for example, sleeves (e.g., tubular sleeves) that are configured to be positioned over inner liner 18 and structural support member 20, and, if present, support layer 22.

Segments of outer jacket 24 are situated longitudinally adjacent to each other, e.g., in an abutting relationship, and, in some examples, can be mechanically connected together to define outer jacket 24 using any suitable technique, such as by welding, an adhesive, heating/reflow, or any combination thereof. Adjacent outer jacket segments of outer jacket 24 form a junction between the adjacent outer jacket segments. Segments of outer jacket 24 may each have any suitable length, which may be selected based on the desired flexibility profile of catheter body 12. In some examples, proximal, distal, and intermediate portions 17A-17C (FIG. 1) of catheter body 12 may have their own respective outer jacket segments that each begin and end at the proximal and distal ends of the corresponding catheter body portions 17A-17C. In other examples, one of the outer jacket segments may extend at least over both proximal portion 17A and intermediate portion 17C, and/or over both intermediate portion 17C and distal portion 17B.

In some examples, the composition of each of segments 24A and 24B may be selected to at least partially provide the catheter body with desired flexibility characteristics. For example, different materials may have different properties, such as durometer, compressibility, elasticity, and the like. The stiffness and/or hardness (e.g., durometer) of outer jacket 24 contribute to the flexibility and structural integrity of the catheter body. Accordingly, the composition and properties of each of segments 24A and 24B of outer jacket 24, such as durometer and/or thickness, may be selected to assist in providing portion 40 of the catheter body with the desired flexibility characteristics.

In some examples, at least two outer jacket segments of outer jacket 24 are formed from different materials (e.g., materials having different chemical compositions and/or different material characteristics). Example materials for segments 24A and 24B of outer jacket 24 include, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, South Carolina), another thermoplastic elastomer or other thermoplastic material, or combinations thereof. In one example, a more proximal segment, such as segment 24A, is formed from an aliphatic polyamide and a more distal segment, such as segment 24B, is formed from a polyether block amide. The compositions of the polyether block amide may be modified to achieve segments having different durometers.

In some examples, the durometers of each of segments 24A and 24B may be selected to help provide the catheter body with the desired flexibility characteristics. For example, at least two outer jacket segments of outer jacket 24 may have different durometers. In some examples, segments of outer jacket 24 may have a durometer between about 30 A-100 A or 25D and about 90D. In other examples, however, one or more of the segments of outer jacket 24 may have other hardness values. The hardness of the segments of outer jacket 24 may be selected to obtain more or less flexibility, torqueability, and pushability for all or part of the catheter body. In some examples, such as example portions of the catheter body in which the catheter body increases in flexibility from proximal end 32A towards distal end 32B, the durometer of two adjacent outer jacket segments of outer jacket 24 may decrease in a direction from a proximal end of outer jacket 24 towards a distal end. For example, a durometer of first outer jacket segment 24A may be greater than a durometer of second outer jacket segment 24B. As a result, the catheter body may be more flexible for navigating catheter 10 through vasculature of a patient.

In some examples, such as example portions of the catheter body in which the catheter body decreases in flexibility along any part of the catheter body between from proximal end 32A towards distal end 32B, the durometer of two adjacent outer jacket segments of outer jacket 24 may increase in a direction from a proximal end of outer jacket 24 towards a distal end. For example, a durometer of first outer jacket segment 24A may be less than a durometer of second outer jacket segment 24B. While it may be desirable in some cases to provide a catheter body having a relatively flexible distal portion, as explained above, increasing the durometer of a distal-most section of outer jacket 24 relative to a more proximal section that is directly adjacent to the distal-most section, may provide certain advantages. For example, increasing the durometer of the distal-most section may configure a distal opening (e.g., distal opening 13 of FIG. 1) of the catheter body (e.g., catheter body 12 of FIG. 1) to resist geometric deformation when distal opening 13 of catheter body 12 is engaged with a guidewire, which may help support the navigation of catheter body 12 through vasculature. The distal-most section of outer jacket 24 that exhibits the increased stiffness may be a relatively small length of the catheter body and, therefore, may not affect the overall flexibility of the catheter body.

In some examples, structural support member 20 may be configured to help provide catheter body 24 with desired flexibility characteristics. For example, structural support member 20 may include one or more portions that includes different properties related to a flexibility of the catheter body. In some examples, structural support member 20 includes structures having different physical parameters, including different pitches and/or different diameters, to help provide desired flexibility characteristics to the catheter body. For example, decreasing a density of structural support member 20 and/or decreasing a diameter of structural support member 20 may correspond to an increase in flexibility of a corresponding portion 32B of the catheter body. A decreasing density of structural support member 20 may correspond to an increasing pitch (e.g., spacing between coils or braids) of structural support member 20. In some examples, a pitch of structural support member may be between about 0.00225 inches (about 0.057 mm) to about 0.0070 inches (about 0.018 mm).

In some examples, structural support member 20 includes different intrinsic properties modified by heat treatment, including different residual stress or ductility, to help provide desired flexibility characteristics to the catheter body. For example, various physical parameters of structural support member 20, such as density and/or diameter, or outer jacket 24, such as durometer or thickness, may be at or near a limit, such that density and/or diameter of structural support member 20 and/or durometer or thickness of outer jacket 24 may not be decreased further without adversely affecting other properties of the catheter body. To provide further flexibility to the catheter body, one or more portions of structural support member 20 may be heat treated to reduce a residual stress and/or increase a ductility of structural support member 20 and, correspondingly, a flexibility of a portion of the catheter body. The heat treatment may help provide a desired flexibility to the catheter body from structural support member 20.

As one example, during fabrication of catheter 10, springback forces, especially at a distal end of structural support member 20, such as second portion 20B, may cause structural support member 20 to resist conformance to an inner liner 18 of a subassembly of catheter 10. Without a reduced residual stress or increased ductility of structural support member 20, structural support member may require an adhesive to lay flat against inner liner 18, which may increase thickness of a corresponding outer jacket 24, or may not lay flat against inner liner 18, which may reduce integrity of structural support member 20 into catheter 10. However, the reduced residual stress and/or higher ductility of second portion 20B of structural support member 20 may permit greater conformance with an underlying inner liner 18 and/or mandrel, such that second portion 20B may more easily remain positioned against inner liner 18 and/or the mandrel during assembly of catheter 10, thereby better integrating structural support member 20 into catheter 10.

As another example, during navigation of catheter 10 through vasculature of a patient, resistance to bending of the catheter body may exert compressive forces on an inside radius of the catheter body, such as at portion 40. Without variable residual stress or ductility structural support member 20, structural support member 20 may have a flexibility that may be limited by a density and diameter of structural support member 20, and the compressive forces may cause portion 40 to kink or buckle in or near second portion 20B. However, the lower residual stress and/or higher ductility of second portion 20B of structural support member 20 may permit greater deflection, such that second portion 20B may bend rather than compressing against a wall of the vasculature and continue navigation without an increase in compressive forces that cause kinking or buckling.

As another example, the catheter may include a radiopaque marker 38 at a distal end of the catheter body, as shown in FIG. 5A. Radiopaque marker 38 may have lower flexibility than outer jacket segment 24B, such that presence of radiopaque marker 38 may displace at least a portion of outer jacket segment 24B and decrease a flexibility of the distal end. To at least partly compensate for this reduction in flexibility of outer jacket 24, second portion 20B of structural support member 20 may be heat treated to decrease residual stress or increase a ductility of second portion 20B, such that the overall flexibility of distal portion 32B of the catheter body may be relatively unchanged.

In some examples, structural support member 20 may taper and/or expand at various portions, such as portion 40, of catheter body 12. As illustrated in the example portion 40 of FIGS. 5A-5C, structural support member 20 tapers from a first diameter at proximal portion 32A to a second diameter at distal portion 32B. For example, structural support member 20 may taper from a first, larger coil diameter to a second, smaller coil diameter. The diameter can be measured, for example, an inner diameter of structural support member 20 and/or an outer diameter of structural support member 20. In the example shown in FIGS. 5A-5C, proximal portion 20A of structural support member 20 has a first coil outer diameter and distal portion 20B of structural support member 20 has a second coil outer diameter that is smaller than the first coil outer diameter, such that structural support member 20 tapers from the first coil outer diameter to the second coil outer diameter.

In other examples in which inner liner 18 also tapers from a first outer (and/or inner) diameter to a second outer (and/or inner) diameter (smaller than the first outer (and/or inner) diameter), examples in which catheter body 12 tapers from a first outer diameter to a second outer diameter, or both, structural support member 20 may taper to follow the change in the outer diameter of inner liner 18, catheter body 12, or both inner liner 18 and catheter body 12.

In some examples, at least two outer jacket segments of outer jacket 24 have different thicknesses or diameters. For example, a lower diameter portion of structural support member 20, such as a smaller diameter distal portion, may have increased flexibility and may enable a thicker outer jacket having a lower durometer, and therefore more flexible, material, while also enabling the catheter to maintain a relatively constant inner diameter of inner liner 18 and outer diameter of outer jacket 24.

In some examples, such as examples in which structural support member 20 decreases in outer diameter (e.g., tapers) from proximal end 12A towards distal end 12B as illustrated in FIG. 1, the thickness of each of outer jacket segments 60 may increase in a direction from a proximal end of outer jacket 24 towards a distal end. For example, outer jacket 24 may expand from a first inner diameter to a second, larger inner diameter. In the example shown in FIGS. 5B and 5C, proximal outer jacket segment 24A has a first jacket inner diameter and distal outer jacket segment 24B has a second jacket inner diameter, such that outer jacket 24 expands from the first jacket inner diameter to the second jacket inner diameter. As a result, a thickness of proximal outer jacket segment 24A may be less than a thickness of distal outer jacket segment 24B. In some examples, such as examples in which catheter body 12 tapers in outer diameter proximate to distal end 12B as shown in FIG. 1, the thickness of adjacent outer jacket segments of outer jacket 24 may decrease in a direction from the proximal end of outer jacket 24 towards the distal end. For example, a thickness of first outer jacket segment 24A may be greater than a thickness of second outer jacket segment 24B. In some examples, at least two segments of outer jacket 24 may also define different inner diameters than each other, where the inner diameter of a particular segment of outer jacket 24 may be selected to accommodate the portion of catheter body 12 in which a sleeve corresponding to the segment 60 is to be positioned. In some examples, each segment of outer jacket 24 has the same wall thickness (measured in a direction orthogonal to longitudinal axis 16 (FIG. 1). In other examples, the wall thicknesses of segments of outer jacket 24 may differ.

FIGS. 6-9 illustrate systems and methods for forming catheters described herein. Some example catheters described herein may include a structural support member that has been heat treated prior to complete assembly of the catheter. For example, a structural support member having a relatively low diameter may have a high amount of cold work due to drawing or other forming methods that create a large amount of deformation to achieve the relatively low diameter. To increase adhesion of the structural support member to an inner liner of the catheter, the structural support member may be positioned on the inner liner and heat treated to reduce the stiffness of the structural support member and fix the structural support member to the inner liner.

Figure 6:
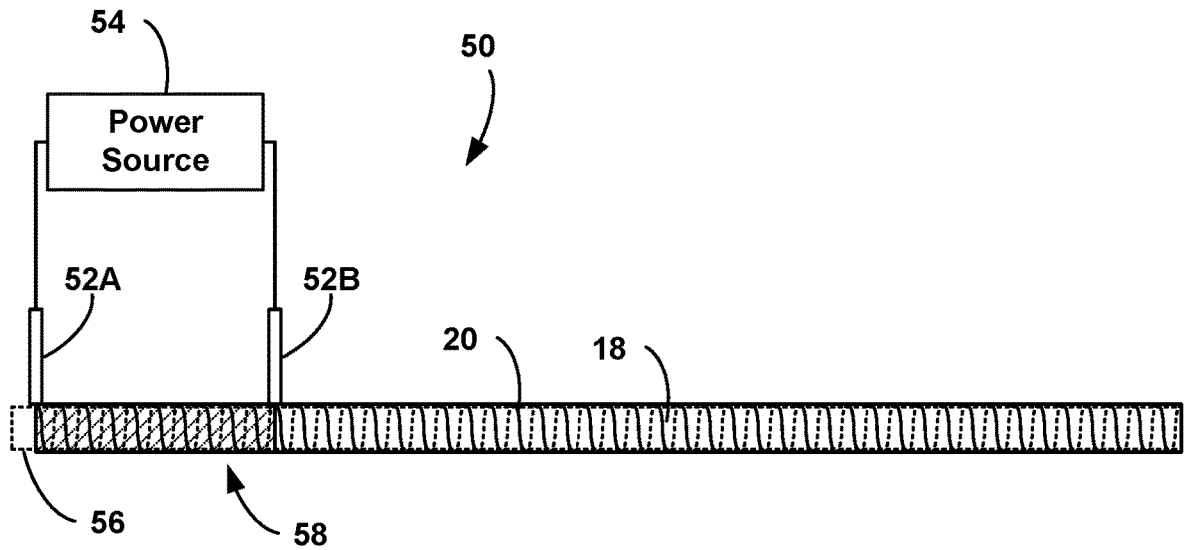
FIG. 6 is a conceptual schematic diagram of an example system for forming the catheters of FIGS. 1-5.

FIG. 6 is a conceptual schematic diagram illustrating an example system for forming the catheters of FIGS. 1-5. System 50 is configured to increase a flexibility of one or more portions of catheter body 12 by heat treating a corresponding portion of structural support member 20 prior to catheter 10 being assembled. In some examples, system 50 includes a mandrel 56 configured to position and/or stabilize inner liner 18 and structural support member 20 within system 50. For example, mandrel 56 may be configured to fit within inner liner 18 and structural support member 20, such that mandrel 56 may be sized to an inner diameter of catheter 10.

System 50 includes one or more contact elements 52A and 52B coupled to a power source 54. Contact elements 52A and 52B may be configured to heat one or more portions 58 of structural support member 20 to decrease residual stress and/or increase ductility of a corresponding portion of structural support member 20. For example, contact elements 52A and 52B may be configured to receive electricity from power source 54 and create a circuit through portion 58 of structural support member 20 to heat portion 58 of structural support member 20, such as through joule heating. In some example, contact elements 52A and 52B may be configured to provide localized heat treatment to particular portions 58 of structural support member 20.

Figure 7:
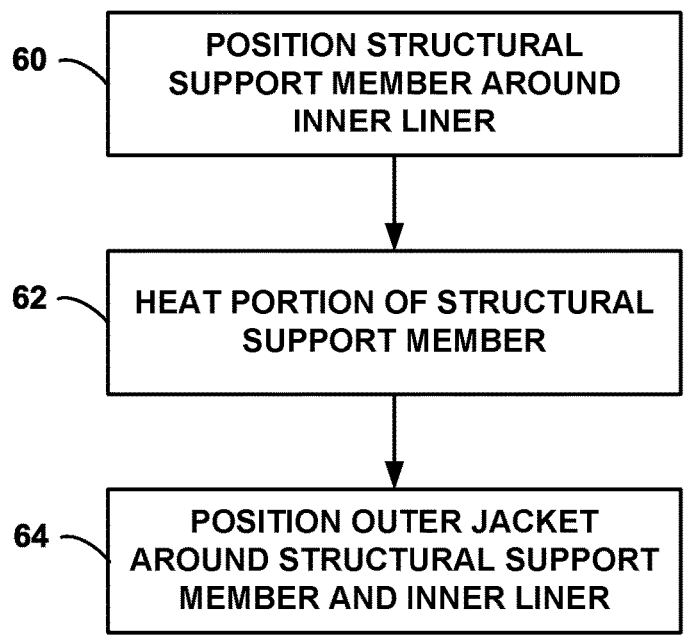
FIG. 7 is a flow diagram of an example method of forming the catheters of FIGS. 1-5.

FIG. 7 is a flow diagram of an example method of forming the catheters of FIGS. 1-5 having a heat-treated structural support member, such as any of catheter 10 of FIGS. 1 and 2, portion 30 of FIG. 3, and/or portion 40 of FIGS. 5A-5C, and will be described with reference to catheter 10 of FIG. 1 and system 50 of FIG. 6.

At any time prior to positioning structural support member 20 over inner liner 18 (60), inner liner 18 may be positioned over mandrel 56. In some examples, inner liner 18 may be positioned over mandrel 56 by at least inserting mandrel 56 through an end of inner liner 18. After positioning inner liner 18 over mandrel 56, structural support member 20 may be positioned over inner liner 18 (60). In examples in which structural support member 20 includes a coil member, the wire defining the coil member may be wound over an outer surface of inner liner 18 or pushed over inner liner 18. The coil member can be, for example, a single coil member that is devoid of any joints. In some examples, the structural configuration of structural support member 20 may be at least partially defined as it is wound over inner liner 18 in some examples. For example, a shape memory wire or a stainless steel wire may be wound over inner liner 18 to define the desired coil pitch, the desired diameter(s), the desired taper, the desired length, or any combination thereof of member 20. The shape memory wire may then be heat set to define structural support member 20.

In some examples, the structural configuration of structural support member 20 may be at least partially defined prior to being positioned over inner liner 18. For example, a shape memory wire (e.g., a nickel-titanium wire) or a wire of an otherwise heat-settable metal or alloy may be wound over a different mandrel (e.g., a "coil mandrel") on which inner liner 18 is not present or over the mandrel (e.g., before inner liner 18 is positioned on the mandrel) to define at least one of the desired coil pitch, the desired coil diameter, the desired tapering profile (e.g., a continuous tapering or progressive tapering), or the desired length of structural support member 20, and then heat set to substantially hold its shape. The wire may then be subsequently unwound from the mandrel onto a reel or a bobbin, and then positioned over inner liner 18. Structural support member 20 may be positioned over inner liner 18 by, for example, winding structural support member 20 over inner liner 18 (e.g., winding member 20 from the bobbin or reel onto inner liner 18) or by pushing inner structural support member 20 over an end of inner liner 18.

In some examples, a wire formed from a shape memory metal/alloy or an otherwise heat-settable metal/alloy may be preformed into a helical coil having a constant pitch and the desired diameters, including the desired taper, and then, once positioned over inner liner 18, the layout of the coiled wire may be adjusted to achieve the desired pitch profile (e.g., the change in pitch over the length) of structural support member 20. For example, the pitch of the wire may be adjusted over inner liner 18 to achieve the desired pitch profile. These adjustments may be made manually, by hand, or by a computer-controlled device. In other examples, however, a wire may be preformed into a helical coil having the desired pitch profile and diameters for structural support member 20 before being positioned over inner liner 18.

Defining some or all of the structural characteristics of structural support member 20 prior to positioning structural support in member 20 over inner liner 18 may help control the structural characteristics of structural support member 20, as well as control the uniformity of the structural support member 20 of multiple catheter bodies. Pre-shaping and shape-setting the member 20 as a coil (as opposed to ordinary wire stock) causes the member 20 to conform closely to the inner liner 18 as the member 20 is wound onto the liner 18. This close conformance, on its own and in combination with the resulting reduced need for adhesives or other measures to keep the wound member in place on the liner 18, helps reduce the wall thickness T in the catheter body 12. In addition, shape-setting the structural support member 20 on a separate, heat-resistant mandrel enables the construction of the catheter body 12 using the member 20 on a mandrel made of PTFE or other lubricious, non-heat resistant material.

Structural support member 20 may be secured in place relative to inner liner 18 using any suitable technique. In some examples, outer jacket 24 may at least partially secure structural support member 20 to inner liner 18. In some examples, an adhesive and/or a polymer, such as support layer 22, may be used to secure structural support member 20 to inner liner 18. As noted above, in some examples, catheter body 12 includes support layer 22. To form support layer 22, a layer of a thermoplastic or a thermoset polymer may be applied over structural support member 20 after structural support member 20 is positioned over inner liner 18, while in other examples, a layer of a thermoplastic or a thermoset polymer may be applied over inner liner 18 prior to positioning structural support member 20 over inner liner 18. The thermoset polymer may be, for example, a viscoelastic thermoset polyurethane (e.g., Flexobond 430). At least some of the polymer may be positioned between the turns of the wire defining structural support member 20. Positioning the thermoset polymer over inner liner 18 and structural support member 20 in this manner may help bond inner liner 18 and structural support member 20 to outer jacket 24 through support layer 22. For example, the polymer may contact surfaces of structural support member 20, including surfaces of structural support member 20 having a surface treatment, and provide a surface for bonding to outer jacket 24. In contrast, depositing a polymer over inner liner 18 prior to positioning structural support member 20 may lead to surfaces of structural support member 20 void of the polymer, where such surfaces may not as readily or strongly bond with outer jacket 24 as surfaces of support layer 22. After the polymer is positioned over inner liner 18 and structural support member 20 (not shown), the polymer is cured (not shown), e.g., by heating and/or time-curing. In other examples, the polymer can be cured after outer jacket 24 is positioned over inner liner 18, structural support member 20, and the polymer.

In accordance with the technique shown in FIG. 7, structural support member 20 is heat treated by at least applying a heat treatment to at least a portion of structural support member 20 to decrease residual stress and/or increase ductility of structural support member 20 at the corresponding portion of structural support member 20 (62). In some examples, the heat treatment is applied to the entire structural support member 20. In other examples, such as illustrated in FIG. 6, the heat treatment is applied to only a portion 58, such that other portions of structural support member 20 remain untreated in the same manner. For example, referring to FIG. 3, the heat treatment may be applied to distal portion 20C of structural support member 20 such that, after heat treating, distal portion 20C of structural support member 20 has a first amount of residual stress and proximal portion 20A of structural support member 20 has a second amount of residual stress, greater than the first amount of residual stress. In other examples, the heat treatment is applied to portions of structural support member 20 in a different manner, such that various portions of structural support member 20 may have varying degrees of heat treatment. For example, referring to FIG. 3, the heat treatment may be applied to distal portion 20C of structural support member 20 at a higher first degree (e.g., at a higher temperature and/or for a longer period of time) and to medial portion 20B of structural support member 20 at a lower second degree (e.g., at a lower temperature and/or for a shorter period of time) such that, after heat treating, distal portion 20C of structural support member 20 has a first amount of residual stress and medial portion 20B of structural support member 20 has a second amount of residual stress, greater than the first amount of residual stress, though less than an amount of residual stress of any untreated portions of structural support member 20.

In some examples, structural support member 20 may be secured in place relative to inner liner 18 using heat treatment processes of structural support member 20 described herein. For example, structural support member 20 may have a high amount of cold work due to drawing or other forming methods that create a large amount of deformation, such that structural support member 20 may be relatively stiff. As a result of this stiffness, structural support member 20 may be relatively difficult to position on inner liner 18 without an adhesive. To increase adhesion of structural support member 20 to inner liner 18, a portion of structural support member 20 may be heat treated to reduce the stiffness of the portion of structural support member 20 and fix structural support member 20 to inner liner 18, thereby reducing or eliminating an adhesive to secure structural support member to inner liner 18 and/or outer jacket 24.

A variety of heating techniques may be used to apply the heat treatment to one or more portions of structural support member 20. In some examples, applying the heat treatment may include by applying an electrical current through a portion of structural support member 20 to heat the portion of structural support member 20. For example, as illustrated in FIG. 6, contact elements 52A and 52B may contact structural support member 20 to complete a circuit and define portion 58 of structural support member 20 through which current may flow. Power source 54 may supply electrical current through portion 58 to generate joule heating in portion 58 of structural support member 20. In this way, heat may be relatively limited to a particular portion of catheter 10.

In some examples, heat treatment of one or more portions of structural support member 20 may involve heating the one or more portions of structural support member 20 to a heat treatment temperature, maintaining the one or more portions of structural support member 20 at or above the heat treatment temperature for a period of time, and optionally cooling the one or more portions of structural support member 20. In some examples, the heat treatment temperature may be greater than about 300° C.

In some examples, the heat treatment may include applying heat to structural support member 20 to achieve a particular heat treatment temperature of a portion of structural support member 20. In some examples, the heat treatment may include annealing, such that heat treating a portion of structural support member 20 includes heating at least a portion of the elongated body to heat the portion of structural support member 20 to a temperature above a recrystallization temperature of structural support member 20. Annealing includes any heat treatment that involves heating up to and maintaining a temperature of a portion of structural support member 20 above a recrystallization temperature of a material of structural support member 20 for a period of time. As a result of annealing, an annealed portion of structural support member 20 may have a higher ductility and/or lower hardness than a portion of a similar structural support member (e.g., another portion of structural support member 20) that is not annealed or annealed to a lesser extent. In some examples, the heat treatment may involve other heat treatments that involve temperatures below a recrystallization temperature of a material of structural support member 20. For example, structural support member 20 formed from nitinol (recrystallization temperature of between about 450° C. and about 550° C.) may be heat treated at temperatures below 450° C., such as about 300° C., to increase percent elongation and/or reduction in area at fracture of the portion of structural support member 20.

In some examples, the heat treatment may include maintaining structural support member 20 at or above the particular heat treatment temperature for a period of time. For example, a reduction in residual stress in a portion of structural support member 20 may correspond to an amount of time the portion of structural support member 20 is heated, such that a longer heat treatment time may correspond to a greater reduction in percent cold work. In some examples, the heat treatment may include cooling at least the catheter body to cool the first portion of structural support member 20 to a temperature below the recrystallization temperature of structural support member 20. For example, catheter body 12 may be actively or passively cooled to achieve a particular cooling rate.

In some examples, applying the heat treatment includes applying the heat treatment to, or in various amounts at, particular portions of structural support member 20 to increase flexibility of the corresponding portion of catheter body 12. These one or more portions that are heat treated can be certain portions of structural support member 20 that may be more likely to experience stresses that can cause deflection or other deformation than other portions of structural support member 20. For example, a first portion of structural support member 20, such as a more distal portion that may experience a higher degree of tortuosity that more proximal portions, may be heat treated, and a second portion of structural support member 20, such as a more proximal portion, may not be heat treated. As a result, the first portion of structural support member 20 may have different properties than the second portion of structural support member 20. For example, the first portion of structural support member 20 may have a first ductility and the second portion of structural support member 20 may have a second ductility that is greater than the first ductility.

In some examples, one or more portions of structural support member 20 that may be subject to relatively high deformation during navigation to a treatment site may be heat treated. For example, a first portion of structural support member 20 may be heat treated to decrease residual stress and/or increase a ductility of the first portion of structural support member 20, such that the first portion of structural support member 20 may more easily conform to inner liner 18 during assembly and/or navigate through the vasculature, while a second portion of structural support member 20 may not be heat treated, or may be heat treated to a lesser extent than the first portion of structural support member 20. In some examples, a distal portion of structural support member 20 may be heat treated, such as a distal-most five centimeters from distal end 12B. In some examples, one or more portions of structural support member 20 that may be subject to relatively high deformation during treatment may be heat treated. For example, a first portion of structural support member 20 may be heat treated to decrease residual stress and/or increase a ductility of the first portion of structural support member 20, such that the first portion of structural support member 20 may more easily conform to the vasculature without kinking.

In some examples, one or more portions of structural support member 20 adjacent to relatively inflexible components may be heat treated. For example, a first portion of structural support member 20 near distal opening 13 may be adjacent to a radiopaque marker or other functional component that has a flexibility lower than support layer 22 and/or outer jacket 24, such that a thickness of outer jacket 24 adjacent to the first portion of structural support member 20 may be less than a thickness of outer jacket 24 adjacent to a second portion of structural support member 20. To compensate for the relatively low thickness of outer jacket 24, the first portion of structural support member 20 may be heat treated, such that the first portion of structural support member 20 has a lower residual stress and/or higher ductility than the second portion of structural support member 20.

After at least a portion 58 of structural support member 20 is heated (62), outer jacket 24 may be positioned over an outer surface of structural support member (64). During and/or after positioning outer jacket 24, material of outer jacket 24 may be flowed and/or reflowed between structures (e.g., coils or braids) of structural support member 20, such that at least a portion of a volume between the structures of structural support member 20 may be filled with the material of outer jacket 24. In some instances, the material of outer jacket 24 may contact inner liner 18 to form an interface between inner liner 18 and outer jacket 24. This interface may provide adhesion between inner liner 18 and outer jacket 24, in addition to adhesion between structural support member 20 and inner liner 18 or outer jacket 24. Regardless of whether inner liner 18 and outer jacket 24 form an interface, outer jacket 24 may provide longitudinal support for structural support member 20, such that outer jacket 24 may at least partially limit movement of structural support member 20 between inner liner 18 and outer jacket 24. In this way, outer jacket 24 may assist in integrating structural support member 20 into catheter body 12.

In some examples, outer jacket 24 is adhered to an outer surface of structural support member 20, e.g., an adhesive and/or a polymer may be applied to outer surface of member 20 prior to positioning outer jacket 24 over member 20 and then cured after outer jacket 24 is positioned over member 20. In addition to, or instead of, the adhesive, outer jacket 24 may be heat shrunk over member 20 and inner liner 18. In some examples, the heat shrinking of outer jacket 24 helps secure member 20 in place relative to inner liner 18.

In some examples, such as illustrated in FIGS. 5A-5C, outer jacket 24 may include a plurality of outer jacket segments, such that positioning outer jacket 24 over structural support member 20 and inner liner 18 may include positioning a plurality of sleeves around structural support member 20 and inner liner 18. For example, each sleeve may be slid over the outer surface of member 20 and positioned longitudinally adjacent to at least one other sleeve. Each sleeve of the plurality of sleeves may correspond to one or more outer jacket segments. The sleeves may have different compositions and/or properties. For example, at least two sleeves may have different materials, different durometers, and/or different thicknesses. In some examples, a sequence in which the sleeves may be positioned may define increasing or decreasing flexibility of catheter body 12. As one example, to increase flexibility from a proximal to a distal end of portion 30, a durometer of a first sleeve is greater than a durometer of the second sleeve, such that a durometer of first outer jacket segment 24A is greater than a durometer of second outer jacket segment 24B. As another example, to decrease flexibility from a proximal to a distal end of portion 30, a durometer of first sleeve is less than a durometer of the second sleeve, such that a durometer of first outer jacket segment 24A is less than a durometer of second outer jacket segment 24B.

In some examples, forming outer jacket 24 includes positioning a first sleeve corresponding to first outer jacket segment 24A over structural support member 20 and positioning a second sleeve corresponding to second outer jacket segment 24B over structural support member 20, distal to the first sleeve. After positioning outer jacket segments of outer jacket 24, outer jacket segments 24A and 24B may be mechanically connected together at a junction and configured to substantially conform to the outer surface of structural support member 20, inner liner 18, and/or a support layer (not shown) using any suitable technique. In some examples, segments of outer jacket 24 are formed from a flowable/reflowable material. Heat may be applied to segments of outer jacket 24 to cause at least a portion of segments of outer jacket 24 to melt and flow into spaces between structures of structural support member 20. The heat may cause segments of outer jacket 24 to at least partly fuse together to define a substantially continuous outer jacket 24. The use of heat to apply outer jacket 24 to the subassembly including inner liner 18 and structural support member 20 may help eliminate the need for an adhesive and/or support layer between structural support member 20 and outer jacket 24.

In some examples, segments of outer jacket 24 are formed from a heat shrinkable material. A heat shrink tube may be positioned over segments of outer jacket 24, and heat may be applied to cause the heat shrink tube to wrap tightly around segments of outer jacket 24. The heat and wrapping force may cause segments of outer jacket 24 to fuse together to define a substantially continuous outer jacket 24. The heat shrunk tube may then be removed from the assembly, e.g., via skiving or any suitable technique. The use of heat shrinking to apply outer jacket 24 to the subassembly including inner liner 18, a support layer (optional and not shown), and structural support member 20 may help eliminate the need for an adhesive between structural support member 20 and outer jacket 24.

In some examples, as will be described with reference to FIG. 1 unless otherwise indicated, a method of using catheter 10 includes introducing catheter 10 into vasculature (e.g., an intracranial blood vessel) of a patient via an access point (e.g., a femoral artery or a radial artery), and guiding catheter body 12 through the vasculature. In some instances, catheter body 12 may encounter tortuous vasculature that exerts a bending or compressive force on catheter body 12 in response to a pushing or rotating force at a proximal end of catheter 10. As catheter body 12 is advanced through the tortuous vasculature, catheter body 12 may resist kinking or buckling. As one example, as illustrated in FIG. 2, structural support member 20 may more easily deflect in response to tortuous vasculature, at least partly due to reduced residual stress and/or increased ductility from one or more heat-treated portions of structural support member 20. As another example, as illustrated in portion 30 of FIG. 3, structural support member 20 may provide for greater variation in residual stress and/or ductility, and therefore flexibility, along catheter body 12, such as according to heat treatment profile 31. As another example, as illustrated in portion 40 of FIGS. 5A-5C, structural support member 20 may provide for greater variation in flexibility and/or compressibility in combination with other components of catheter body 12. In these various ways, catheter body 12 may have increased flexibility and/or pushability of catheter 10 through tortuous vasculature of a patient. Any of the examples of catheter body 12 characteristics that contribute to a resistance to kinking, buckling, or springback can be used in combination with each other.

Once distal end 12B of catheter body 12 is positioned at the target tissue site, which may be proximal to thromboembolic material (e.g., a thrombus), the thromboembolic material be removed from the vasculature via catheter body 12. For example, the thromboembolic material may be aspirated from the vasculature by at least applying a vacuum force to inner lumen 26 of catheter body 12 via hub 14 (and/or proximal end 12A), which may cause the thromboembolic material to be introduced into inner lumen 26 via distal opening 13. Optionally, the vacuum or aspiration can be continued to thereby draw the thromboembolic material proximally along the inner lumen 26, all or part of the way to the proximal end 12A or hub 14. As a further option, the aspiration or vacuum may cause the thromboembolic material to attach or adhere to the distal tip; in such a case the catheter 10 or catheter body 12 and the thromboembolic material can be withdrawn from the vasculature together as a unit, for example through another catheter that surrounds the catheter 10 or catheter body 12.

As another example, the thromboembolic material may be removed from the vasculature using another technique, such as via an endovascular retrieval device delivered through the inner lumen 26 of the catheter body 12. In such a method the catheter body 12 can be inserted into the vasculature (for example using any technique disclosed herein) and the retrieval device advanced through the inner lumen 26 (or through another catheter, such as a microcatheter, inserted into the vasculature through the inner lumen 26) so that the device engages the thromboembolic material. The retrieval device and the material engaged thereby (together with any other catheter or microcatheter) can then be retracted into the inner lumen 26 and removed from the patient. Optionally, aspiration can be performed with or through the catheter body 12 during retraction of the retrieval device and thromboembolic material into the catheter body 12. The vasculature can comprise the neurovasculature, peripheral vasculature or cardiovasculature. The thromboembolic material may be located using any suitable technique, such as fluoroscopy, intravascular ultrasound or carotid Doppler imaging techniques.

Various aspects of the disclosure have been described. These and other aspects are within the scope of the following claims.

What is claimed is:

1. A catheter, comprising:
   an inner liner;
   an outer jacket; and
   a structural support member positioned between at least a portion of the inner liner and at least a portion of the outer jacket,
   wherein a first portion of the structural support member has a first residual stress and a second portion of the structural support member has a second residual stress, greater than the first residual stress,
   wherein the second portion of the structural support member comprises a percent cold work greater than about 20%, and
   wherein a thermal degradation temperature of at least one of the inner liner or the outer jacket is greater than a heat treatment temperature of the structural support member sufficient to relieve at least a portion of the second residual stress.

2. The catheter of claim 1, wherein the second residual stress is at least 10% greater than the first residual stress.

3. The catheter of claim 1, wherein an entirety of the structural support member comprises a percent cold work greater than about 30%.

4. The catheter of claim 1, wherein the first portion of the structural support member has a first ductility and the second portion of the structural support member has a second ductility, less than the first ductility.

5. The catheter of claim 1,
   wherein the first portion of the structural support member is positioned in a distal portion at a distal end of the catheter, and
   wherein the distal portion of the catheter comprises between about a distal-most 0.5 centimeters to about a distal-most 5 centimeters from the distal end of the catheter.

6. The catheter of claim 1, wherein the structural support member has a consistent chemical composition throughout a volume of the structural support member.

7. The catheter of claim 1, wherein the structural support member comprises at least one of nitinol, stainless steel, or a cobalt-chromium alloy.

8. The catheter of claim 1, wherein the catheter does not include an adhesive between the first portion of the structural support member and the inner liner.

9. A method, comprising:
   heat treating a first portion of a structural support member of an elongated body of a catheter, the elongated body extending between a proximal and a distal end, the elongated body comprising:
      an inner liner defining an inner lumen of the elongated body and extending to the distal end of the elongated body;
      an outer jacket and
      the structural support member, the structural support member being positioned between at least a portion of the inner liner and at least a portion of the outer jacket;
   wherein, after heat treating, the first portion of the structural support member has a first residual stress and a second portion of the structural support member has a second residual stress, greater than the first residual stress, and
   wherein a thermal degradation temperature of at least one of the inner liner or the outer jacket is greater than a heat treatment temperature of the structural support member sufficient to relieve at least a portion of the second residual stress.

10. The method of claim 9, wherein the second residual stress is at least 10% greater than the first residual stress.

11. The method of claim 9, wherein the first portion of the structural support member has a first ductility and the second portion of the structural support member has a second ductility, less than the first ductility.

12. The method of claim 9, wherein the second portion of the structural support member is not heat treated.

13. The method of claim 9, wherein heat treating the first portion of the structural support member comprises heating the first portion of the structural support member to a maximum temperature below a recrystallization temperature of the structural support member.

14. The method of claim 9, wherein heat treating the first portion of the structural support member comprises heating the first portion of the structural support member to a maximum temperature above a recrystallization temperature of the structural support member.

15. The method of claim 9, wherein the first portion of the structural support member is heat treated while the structural support member is positioned around the at least the portion of the inner liner.

16. The method of claim 15, wherein the first portion of the structural support member is heat treated by applying an electrical current through the first portion of the structural support member to heat the first portion of the structural support member.

17. The method of claim 15, further comprising positioning the structural support member around the at least the portion of the inner liner, wherein the structural support member is positioned around the at least the portion of the inner liner without an adhesive.

18. The method of claim 10,
    wherein the first portion of the structural support member is positioned in a distal portion at a distal end of the catheter, and
    wherein the distal portion of the catheter comprises between about a distal-most 0.5 centimeters to about a distal-most 5 centimeters from the distal end of the catheter.

19. The catheter of claim 1, wherein the thermal degradation temperature of at least one of the inner liner or the outer jacket is greater than a recrystallization temperature of the structural support member.

20. The catheter of claim 1, wherein a melting temperature of at least one of the inner liner or the outer jacket is greater than the heat treatment temperature of the structural support member sufficient to relieve at least the portion of the second residual stress.

* * * * *